United States Patent
Bhattacharjee et al.

(10) Patent No.: US 11,185,256 B2
(45) Date of Patent: Nov. 30, 2021

(54) POINT-OF-CARE HAND TREMOR DETECTION SYSTEM

(71) Applicant: INDIAN INSTITUTE OF TECHNOLOGY, GUWAHATI, Guwahati (IN)

(72) Inventors: Mitradip Bhattacharjee, Guwahati (IN); Dipankar Bandyopadhyay, Guwahati (IN); Sunny Kumar, Guwahati (IN)

(73) Assignee: INDIAN INSTITUTE OF TECHNOLOGY, GUTAHATI, Guwahati (IN)

( * ) Notice: Subject to any disclaimer, the term of this patent is extended or adjusted under 35 U.S.C. 154(b) by 62 days.

(21) Appl. No.: 16/324,558

(22) PCT Filed: Aug. 29, 2017

(86) PCT No.: PCT/IN2017/050366
§ 371 (c)(1),
(2) Date: Feb. 10, 2019

(87) PCT Pub. No.: WO2018/216027
PCT Pub. Date: Nov. 29, 2018

(65) Prior Publication Data
US 2021/0015402 A1     Jan. 21, 2021

(30) Foreign Application Priority Data
May 26, 2017   (IN) .............................. 201731018530

(51) Int. Cl.
*A61B 5/11*    (2006.01)
*A61B 5/00*    (2006.01)

(52) U.S. Cl.
CPC .......... *A61B 5/1101* (2013.01); *A61B 5/4082* (2013.01); *A61B 5/6825* (2013.01);
(Continued)

(58) Field of Classification Search
CPC ... A61B 5/1101; A61B 5/4082; A61B 5/6825; A61B 2505/07; A61B 2562/0247; A61B 2562/164
See application file for complete search history.

(56) References Cited

U.S. PATENT DOCUMENTS 3,972,132 A    8/1976  Slomski
4,306,291 A    12/1981 Zilm et al.
(Continued)

FOREIGN PATENT DOCUMENTS

KR    2016/0129470    11/2016

OTHER PUBLICATIONS

International Search Report of PCT Application No. PCT/IN2017/050366, dated Oct. 30, 2018.
(Continued)

*Primary Examiner* — David J. McCrosky
(74) *Attorney, Agent, or Firm* — Pearl Cohen Zedek Latzer Baratz LLP

(57) ABSTRACT

A portable hand tremor detection device has been reported. This device is composed of a detection unit, a flexible pressure sensor, a signal processing unit, and a power supply. The detection unit is composed of the sensor and press-knob. The flexible pressure sensor is a combination of usually spaced apart flexible polymer preferably polydimethylsiloxane, flexible substrate preferably paper, and a conductive coating preferably reduced graphene oxide (RGO). When the users put pressure on the press-knob through the fingers, the flexible pressure sensor actuates and bends so that conductive RGO layers on the flexible substrates come in contact with each other to generate an output current. The electrical circuits in the signal processing unit are laid down in such a manner that the magnitude of this output current varies with the tremor between the fingers, (Continued)

which eventually converted into an electrical signal showing the variation in the hand tremor with time.

7 Claims, 3 Drawing Sheets

(52) U.S. Cl.
CPC ... *A61B 2505/07* (2013.01); *A61B 2562/0247* (2013.01); *A61B 2562/164* (2013.01)

(56) References Cited

U.S. PATENT DOCUMENTS

| | | | |
|---|---|---|---|
| RE34,095 E * | 10/1992 | Padula | G06F 3/03545 178/19.04 |
| 5,562,104 A | 10/1996 | Hochberg et al. | |
| 5,573,011 A | 11/1996 | Felsing | |
| 6,561,992 B1 | 5/2003 | Eberhart et al. | |
| 6,730,049 B2 | 5/2004 | Kalvert | |
| 6,936,016 B2 | 8/2005 | Berme et al. | |
| 7,236,156 B2 | 6/2007 | Liberty et al. | |
| 8,994,657 B2 | 3/2015 | Liberty et al. | |
| 2001/0012932 A1 | 8/2001 | Peer | |
| 2003/0006357 A1 | 1/2003 | Kaiser et al. | |
| 2004/0151218 A1 | 8/2004 | Branzoi et al. | |
| 2005/0234309 A1 | 10/2005 | Klapper | |
| 2014/0303605 A1 | 10/2014 | Boyden et al. | |
| 2015/0321000 A1 | 11/2015 | Rosenbluth et al. | |
| 2016/0259926 A1 | 9/2016 | åstrand et al. | |
| 2016/0262670 A1 | 9/2016 | Leverett et al. | |

OTHER PUBLICATIONS

Silberberg D., Katabira E. "Neurological Disorders. Disease and Mortality in Sub-Saharan Africa". 2$^{nd}$ edition, Washington (DC): The International Bank for 15 Reconstruction and Development / The World Bank; 2006. Chapter 23.

Neurological disorders: public health challenges. World Health Organization (WHO) 2006.

Beitz, J. M. Frontiers in Bioscience S6, 65-74, Jan. 1, 2014.

Kalia, L. V.; Lang, A. E., Parkinson's disease, Lancet 2015; 386: 896-912.

Crawford, P.; Zimmerman, E. E. Differentiation and Diagnosis of Tremor. American Family Physician. 2011, 83(6):697-702.

Puschmann A, Wszolek Z.K. Diagnosis and Treatment of Common Forms of Tremor. Seminars in 15 neurology. 2011,31(1): 65-77.

* cited by examiner

POINT-OF-CARE HAND TREMOR DETECTION SYSTEM

CROSS-REFERENCE TO RELATED APPLICATIONS

This application is a National Phase Application of PCT International Application No. PCT/IN2017/050366, International Filing Date Aug. 29, 2017, entitled: "POINT-OF-CARE HAND TREMOR DETECTION SYSTEM", which was published on Nov. 29, 2018 under publication number WO 2018/216027, which claims priority of IN Patent Application No., 201731018530, filed May 26, 2017, which is hereby incorporated by reference in its entirety.

FIELD OF THE INVENTION

The present invention is related to detection of hand tremor. More specifically, the present invention is directed to develop a hand tremor detection system for detecting the hand tremor of a person including intensity of the hand tremor. The present system is particularly useful for early detection of different neurological disorders like multiple sclerosis, Parkinson's disease, or Wilson's disease by detecting the hand tremors of the people.

BACKGROUND ART

The hustle and bustle of modern life have made the Neurological diseases to appear every other household and thereby causing serious concerns across the globe [Silberberg D, Katabira E. *Neurological Disorders. Disease and Mortality in Sub-Saharan Africa.* 2nd edition. Washington (D.C.): The International Bank for Reconstruction and Development/The World Bank; 2006. Chapter 23]. Importantly, most of the neurological disorders are almost imperceptible at the early stages because the symptoms are rather obscured as well as transient [*Neurological disorders: public health challenges. World Health Organization (WHO)* 2006, *ISBN* 9241563362]. Thus, in most of the cases, the patient approaches to the medical professionals once the disorder matures to the level of irreversibility. However, many of the common neurological disorders can be prevented if detected in the early stages [*Neurological disorders: public health challenges. World Health Organization (WHO)* 2006, *ISBN* 9241563362]. Among other neurological disorders, Parkinson's disease is one of the most fatal but common in life of the modern human race [Beitz, J. M. *Frontiers in Bioscience* S6, 65-74, Jan. 1, 2014].

One of the very prominent symptoms of Parkinson's disorder is the extent of hand tremor, which remain minimal at the early stages and then magnify as the disease matures [Kalia, L. V.; Lang, A. E., *Parkinson's disease, Lancet* 2015; 386: 896-912]. Notably, the early stage symptoms have been ignored so far in most of the cases owing to the unavailability of the devices that can measure the extent of hand tremor to comprehend the extent of disorder. Furthermore, apart from Parkinson's disease, there are many other neurological disorders that starts with a tremor in the body [Crawford, P.; Zimmerman, E. E. *Differentiation and Diagnosis of Tremor. American Family Physician.* 2011, 83(6): 697-702]. A portable and cost effective point-of-care-testing (POCT) device to detect the early hand tremor can not only cause early detection of the neurological diseases but also can spread awareness on the same and cause prevention.

In human body, tremor is a very common phenomenon, which can be defined as a spontaneous movement of a part of body controlled by the autonomous nervous system. Tremors in the limbs can occur due to many reasons, however, an involuntary tremor is a potential sign of neurological disorders [Puschmann A, Wszolek Z. K. *Diagnosis and Treatment of Common Forms of Tremor. Seminars in neurology.* 2011, 31(1):65-77]. Generally, there the tremors can be classified as normal or abnormal, which has further sub-classes as rest, postural, and intention tremors [Refer to, U.S. Pat. No. 6,561,992 B1]. The rest tremor occurs in a freely hanging limb without voluntary movement and a common symptom for the diseases that involve extra pyramidal system such as the Parkinson's [Refer to, US 2005/0234309 A1]. Intention tremor is related to the intentional movement of the limbs, which increases due to degeneration of the cerebellum and basal ganglia, very often observed for multiple sclerosis, Parkinson's or Wilson's disease [Refer to, U.S. Pat. No. 6,561,992 B1]. The postural tremor happens when limbs are upheld at a place, which increase over a period of time due to the fatigue, anxiety and stress [Refer to, U.S. Pat. No. 6,561,992 B1].

A detailed literature survey indicates that, thus far, there are very few detection techniques available for the tremor measurements of the limbs, which involves accelerometers, motion sensors, or optical and mechanical arrangements [Refer to, U.S. Pat. Nos. 8,994,657, 3,972,132, and 4,306, 291]. Among those detection methods, use of rotational-sensor and accelerometer are the most widely employed. In such devices, a handheld device pointed towards a display-unit helps in detecting the hand tremor by measuring the deviation in rotational axis and vertical displacement using the rotational-sensor and accelerometer [Refer to, U.S. Pat. No. 7,236,156 B2, US 2004/0151218 A1]. The measured deviations are then converted to an electrical signal to correlate the level of tremor. Alternatively, a pressure sensitive pen has also been employed to detect the variation in pressure to measure the hand tremor [Refer to, U.S. Pat. No. 5,562,104]. In this case, the user employs a pen sensitive to the pressure and positions of an electronic tablet to detect the tremor level of the hand of the user. Among the other methodologies, a variable gain amplifier is also employed to detect hand tremor level. In this case, an apparatus generates the signal indicative of tremor and then fed the signal to the amplifier which in turn amplify the received signal [Refer to, U.S. Pat. No. 4,306,291]. Few other reports suggest the detection of body tremor by measuring the load exerted by different body parts wherein the abnormal body tremors are detected using an electronic support surface by measuring the difference in the pressure exerted [Refer to, U.S. Pat. No. 6,936,016 B2, US 2016/0259926 A1]. Use of gyroscope along with the signal analyzer has also been reported in this regard. [Refer to, U.S. Pat. No. 5,573,011]. There are a number of devices also available, which is capable of reducing and controlling the hand tremors [Refer to, US 2015/0321000, U.S. Pat. No. 6,730,049, US 2001/0012932, US 2003/0006357, and US 2014/0303605].

However, the aforementioned detection techniques require either a sophisticated and costly fabrication method or lack portability or limited by the need of medical expertise for analysis. A low-cost and portable system, which can regularly monitor hand tremor and keep a track of any onset of neurological disorder, is found to be absent in the research as well as in the commercial domain.

OBJECT OF THE INVENTION

It is thus the basic object of the present invention is to develop an economic, user-friendly, and portable hand tremor detection system which would be adapted to detect tremor of the user hand.

Another object of the present invention is to develop a portable and point of care hand tremor detection system which would be adapted to facilitate early diagnosis of neurological disorder by measuring level of the hand tremor of the user.

Yet another object of the present invention is to develop a portable hand tremor detection system which can be made by using commercial paper having conductive coating thereon.

Another object of the present invention is to develop a portable hand tremor detection system which would be adapted to wirelessly communicate with peripheral computing device like mobile phone and display the detected hand tremor result on the mobile interface.

Another object of the present invention is to develop a portable hand tremor detection system which would be easy to handle, and can guide the user to measure the fitness of the neurological health in the absence of any medical experts.

SUMMARY OF THE INVENTION

Thus according to the basic aspect of the present invention there is provided a portable hand tremor detection system comprising a grasping means for holding by user with a resiliently biased pressing unit to put pressure on it though fingers when the user holds said grasping mean;

a press sensitive sensor contained within said grasping means having operative communication with said resiliently biased pressing unit comprising of flexible conductors, said flexible conductors maintained usually spaced apart in relaxed condition indicative of no sensor signal and in an actuated condition in contact with one another indicative of generation of hand tremor sensor signal, and an actuator means operatively connected to said flexible conductors for actuating the flexible conductors for said hand tremor based sensor signal generation upon vertical application of pressure on said resiliently biased pressing unit through the user's fingers;

a processing unit for processing said hand tremor based sensor signal for detecting the level of hand tremor of the user; and a cooperative power source.

According to another aspect, the present portable hand tremor detection system comprises said grasping means including a hand tremor detection unit for holding by the user with said resiliently biased pressing unit including a press-knob on said hand tremor detection unit for receiving pressing force of the user;

said flexible pressure sensor contained within said hand tremor detection unit for sensing vertical pressure applied on said press-knob;

said processing unit disposed in operative communication with said paper based pressure sensor to receive output of the sensor and analyzes the same to determine the hand tremor level.

According to yet another aspect in the present portable hand tremor detection system, the flexible pressure sensor is disposed in operative communication with the processing unit through a connecting wire and plug.

According to a further aspect in the present portable hand tremor detection system, the detection unit and the processing unit both contains LEDs for indicating ON-OFF status.

According to another aspect in the present portable hand tremor detection system, the flexible pressure sensor includes a pair of flexible conductive material coated polymer sheet selectively contained in the hand tremor detection unit such that application of the vertical pressure on the press-knob resiliently bends it.

According to another aspect in the present portable hand tremor detection system, the pair of flexible conductive material coated polymer sheet includes two polymer sheets disposed in parallel configuration by a spacer; and conductive coatings on each polymer sheet side facing each other so that upon bending of the polymer sheets, the conductive coating of each polymer sheet of the pair comes in contact to each-other.

According to yet another aspect in the present portable hand tremor detection system, the conductive coatings on the polymer sheets are disposed in operative communication a detection circuit of the processing unit through electrical circuit connector.

According to another aspect in the present portable hand tremor detection system, the polymer sheets are preferably made from polydimethylsiloxane (PDMS) and the conductive coating preferably includes reduced graphene oxide (RGO).

According to a further aspect in the present portable hand tremor detection system, the flexible pressure sensor bends in one direction upon application of the vertical pressure on the press-knob enabling the conductive coatings of the polymer sheets to come in contact with each other and act as an electrical resistor whereby output resistance of said electrical resistor varies with change in the contact area of said conductive coatings.

According a further aspect in the present portable hand tremor detection system, the detection circuit tracks the change in the output electrical resistance and generate electronic signal for correlating with the hand tremor level of the user/person applying vertical pressure on the press-knob.

According to yet another aspect in the present portable hand tremor detection system, the hand tremor detection unit includes a hump structure for providing a mechanical bias the flexible pressure sensor to slightly bent said flexible pressure sensor within housing of the hand tremor detection unit;

an immovable support fixed with housing top of the detection unit;

a movable support attached with said immovable support under bias of a spring.

According to yet another aspect in the present portable hand tremor detection system, the press knob is fixed on the movable support which is attached with housing top of the detection unit under bias of the spring and the immovable support to form the resiliently biased press sensitive sensor unit configured to be compressed under application of the vertical pressure on said press knob which resiliently bend the flexible pressure sensor further while on releasing or decreasing of the pressure, the press-knob moves towards its original position under bias of the spring which relax the flexible pressure sensor, whereby variation in the applied pressure on the press-knob due to hand tremor change bending amount of the flexible pressure sensor which also change the contact area of its conductive coatings resulting a change in the output electrical resistance of the flexible pressure sensor as an indication of the hand tremor.

According to another aspect in the present portable hand tremor detection system, the processing unit includes the detection circuit comprising a network of passive resistor having a supporting resistor ($R_1$) and flexible pressure sensor's contact area resistor ($R_S$) biased with the supply voltage;

an open source electronic development board preferably Arduino UNO; and a short distance communication device preferably Bluetooth module.

According to a further aspect in the present portable hand tremor detection system, the detection circuit transmits the hand tremor indicating electronic signal i.e. the voltage across the network of the supporting resistor ($R_1$) and the flexible pressure sensor's contact area resistor ($R_S$) to the open source electronic development board for converting it into a digital signal.

According to a further aspect in the present portable hand tremor detection system, the communication device forwards the digital signal to a connected display/computing device like mobile phone for further monitoring, processing and storing for future use and reference.

According to another aspect in the present portable hand tremor detection system, the detection circuit transmitted hand tremor indicating electronic signal is the voltage across the flexible pressure sensor's contact area resistor ($R_S$) represented as $$= \left(\frac{R_S}{R_S + R_1}\right) \times V_S$$

wherein, a change in the value of the $R_S$ cause a fluctuation of the voltage.

BRIEF DESCRIPTION OF THE ACCOMPANYING DRAWINGS

DETAILED DESCRIPTION OF THE INVENTION WITH REFERENCE TO THE ACCOMPANYING DRAWINGS

As stated hereinbefore the present invention discloses a portable, point of care hand tremor detection system capable of detecting hand tremor to facilitate early diagnosis of a range of neurological disorders such as the multiple sclerosis, Parkinson's or Wilson's disease, among others.

The present system quantitatively evaluates frequency and magnitude of the hand tremor with the help of an electromechanical sensor arrangement. The present system, includes a grasping means for holding by user with a resiliently biased pressing unit to put pressure on it though fingers when the user holds the grasping means. The grasping means contains a press sensitive sensor having an operative communication with the resiliently biased pressing unit. The press sensitive sensor is configured to translate vertically applied pressure on the resiliently biased pressing unit through the user's fingers into an electronic signal. With the variation in the applied pressure on the pressing unit by the fingers during the hand tremor causes a change in the translated electronic signal which can be correlated in a connected processing unit with the hand tremor level of the user.

Figure 1:
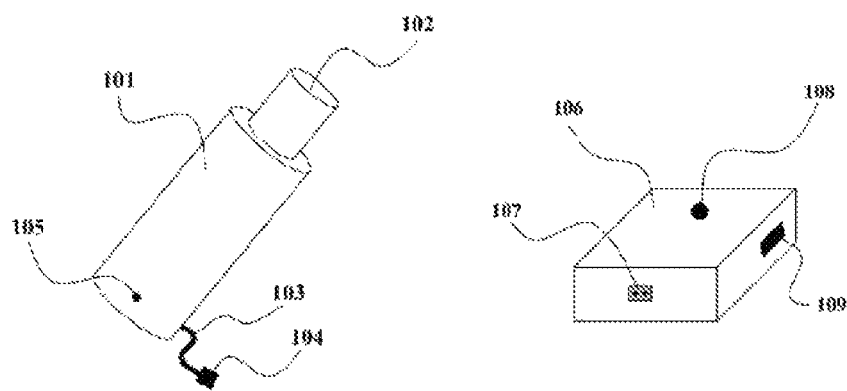
FIG. 1 shows isometric view of the hand tremor detection system in accordance to a preferred embodiment of the present invention.

Reference is first invited from the accompanying FIG. 1, which shows a preferred embodiment of the present system. As shown in the FIG. 1, the present system basically includes a hand tremor detection unit, a flexible pressure sensor, a signal processing unit, and a power supply. The numeral 101 refers to the hand tremor detection unit [i.e. the grasping means] having a press-knob 102 [i.e. the resiliently biased pressing unit] on said hand tremor detection unit 101 which has to be pressed by the user for detection of the tremor. The hand tremor detection unit 101 contains the flexible pressure sensor which is disposed in operative communication with the peripheral signal processing unit 106 through a connecting wire 103 and plug 104.

The signal processing unit 106 contains a socket 107 for connecting with the plug 104 for establishing the operative communication with the flexible pressure sensor to receive output of the sensor and analyzes the same to determine the hand tremor level.

The detection unit 101 and processing unit 106 both contains LEDs 105 and 108 respectively which act as an ON-OFF indicator LEDs for the respective units. The number 109 refers to the ON-OFF switch.

Figure 2:
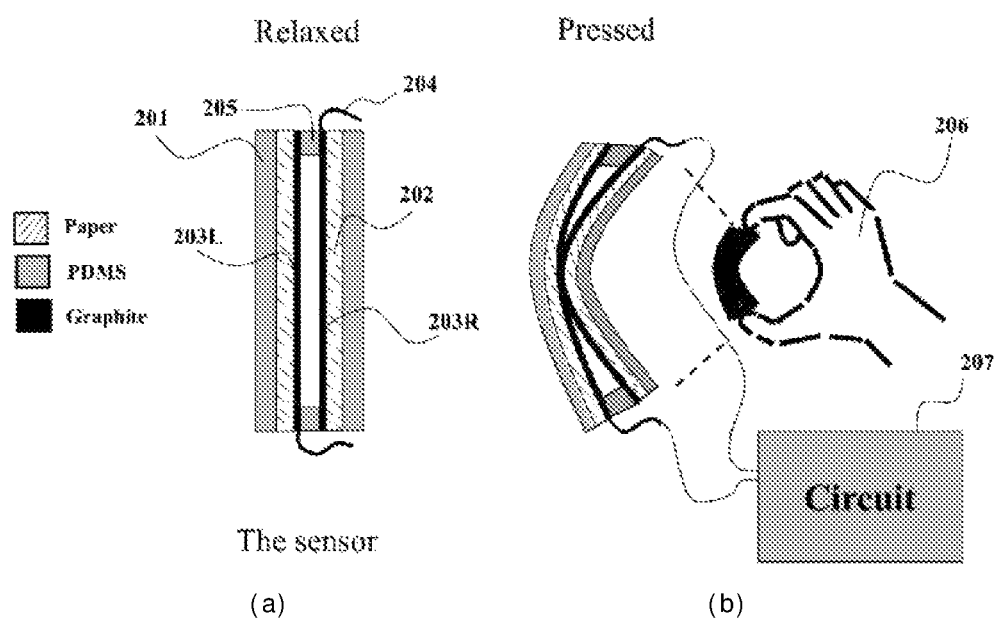
FIG. 2 shows sensor arrangement associated with the hand tremor detection system in accordance to a preferred embodiment of the present invention.

Reference is now invited from the accompanying FIG. 2, which shows the flexible pressure sensor arrangement i.e. press sensitive sensor unit associated with the hand tremor detection system for sensing vertical pressure applied on the press-knob 102.

As shown in the figure, the sensor arrangement includes a pair of flexible conductive material coated polymer sheet (201, 202). The polymer sheets (201, 202) are disposed in parallel configuration with the help of spacer (205) and conductive coatings (203L, 203R) are made on each polymer sheet (201, 202) sides facing each other such that upon bending of the polymer sheets 201,202, the conductive coating of each polymer sheet of the pair comes in contact to each-other.

The polymer sheets 201, 202 are preferably made from polydimethylsiloxane (PDMS) and the conductive coating preferably includes reduced graphene oxide (RGO). The conductive coating (203L, 203R) is disposed in operative communication with detection circuit (207) of the signal processing unit 106 through the electrical circuit connector (204).

The pair of flexible conductive material coated polymer sheet (201, 202) is selectively contained in the hand tremor detection unit 101 such that application of vertical pressure on the press-knob 102 bends the sensor arrangement (as shown in FIG. 2(*b*)).

Upon application of the vertical pressure on the press-knob 102, the polymer sheet pair (201, 202) bends in one direction enabling the conductive coating (203L, 203R) to come in contact with each other and act as an electrical resistor. Output resistance of the electrical resistor varies with the change in the contact area of the conductive coating (203L, 203R). This change in the output electrical resistance is tracked by the detection circuit (207) to generate the electronic signal which for correlating with the hand tremor level of the user/person applying vertical pressure on the press-knob 102. The electronic signal of the sensor goes to the signal processing unit 106 via the detection circuit 207 to measure and display the hand tremor levels.

Figure 3:
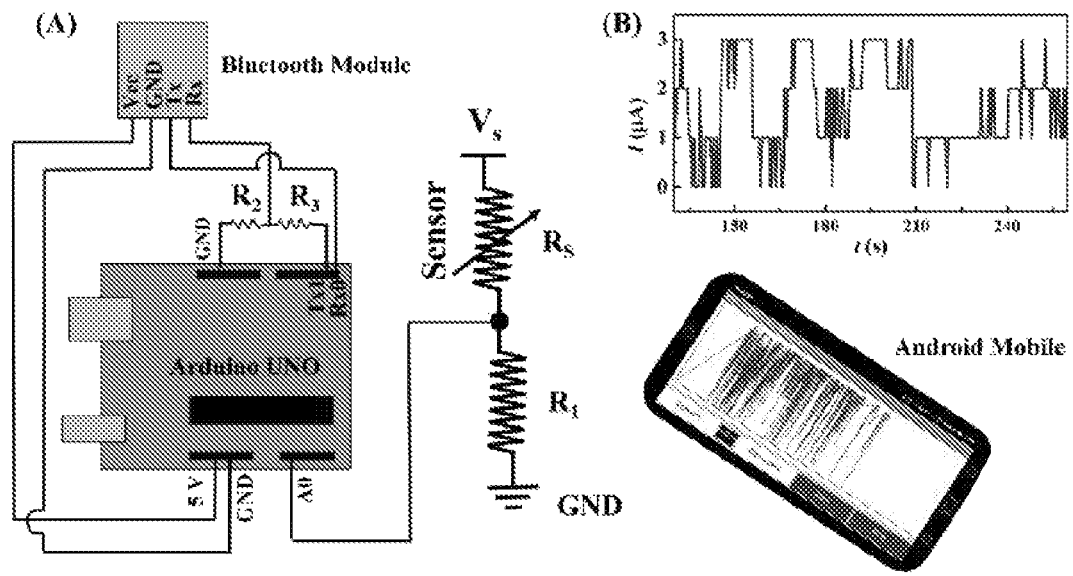
FIG. 3 shows circuit and a typical response of the sensor associated with the hand tremor detection system in accordance to a preferred embodiment of the present invention.

Reference is next invited from the accompanying FIG. 3(A) which illustrates a preferred circuit representation of the signal processing unit 106 including the detection circuit 207. The detection circuit comprises a network of passive resistor comprising a supporting resistor ($R_1$) and sensor's contact area resistor ($R_S$) biased with the supply voltage. The output electronic signal i.e. the voltage across the network of the supporting resistor ($R_1$) and the sensor's contact area resistor ($R_S$) is transmitted to the signal processing unit 106 which comprises an open source electronic development board preferably Arduino UNO, a short distance communication device like Bluetooth module, and resistors $R_2$, and $R_3$. The resistance $R_1$, $R_2$, and $R_3$ are calibrated according to the sensor ($R_S$) response.

The output electronic signal from the detection circuit goes to the analog input pin AO of the open source electronic development board, e.g., Arduino UNO. The signal is then transmitted by the short distance communication device, e.g., Bluetooth module, and is further received by the android mobile application which displays it on the mobile screen. Image (B) shows a typical display on the mobile interface of the current signal from the present system generated due to hand tremor.

To illustrate the working of the detection circuit, the following exemplary situation may be considered.

Considering the value of the supply voltage $V_s$ is 5 V and value of R is 10 kΩ. The resistance of the sensor ¾ changes with the variation in pressure produced due to the tremor. For example, in a particular condition the value of the ¾ changed from say 15 kΩ to 8 kΩ due to the increase in surface area between the two conductive lavers. Thus, the voltage across the sensor ¾, $[=(R_S/(R_S=R_1))<V_S]$ changed from 3 V to 2.22 V. This fluctuation of the voltage goes to the analog input. AO, as shown in the circuit diagram, of the open source electronic development board, e.g., Arduino UNO, and gets converted to a digital signal which can be displayed in a mobile phone display via an app.

Figure 4:
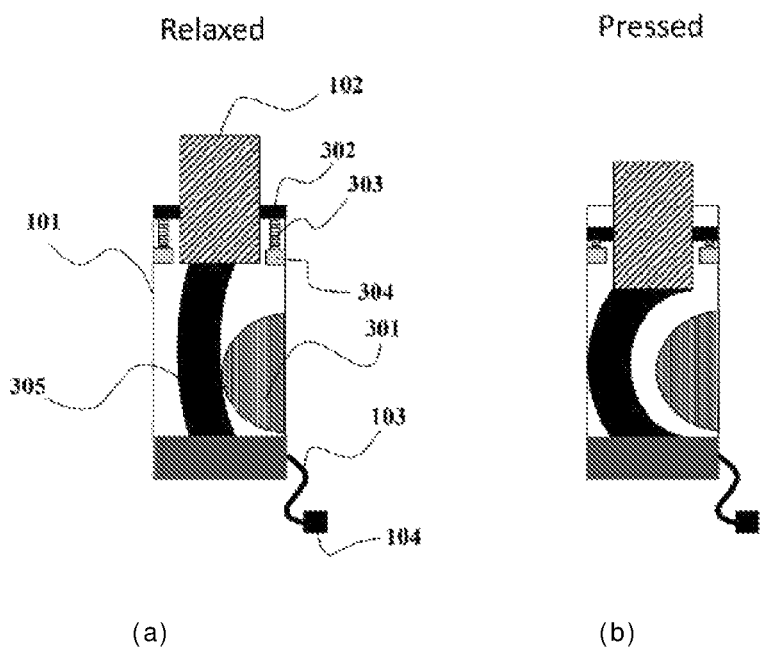
FIG. 4 shows integration of the sensor and cross-sectional view of the hand tremor detection system in accordance to a preferred embodiment of the present invention.

Reference is now invited from the accompanying FIG. 4 which shows the cross-sectional view of detection unit 101. As shown in the FIGS. 4(a) and (b), the press sensitive sensor unit i.e. the flexible pressure sensor 305 is contained with the detection unit 101 under a mechanical bias provided a hump structure 301. This bias makes sure that the sensor 305 will be bent always towards the left side of the detection unit 101 housing. A freely movable support 302 is provided on top of the housing of the detection unit 101 and the press knob 102 is fixed on the movable support 302. The whole arrangement of the movable support 302 and the press knob 102 is attached with the housing top of the detection unit 101 under bias of the spring 303 and an immovable support 304 forming the resiliently biased press sensitive sensor unit. The immovable support 304 is fixed with the housing top of the detection unit 101. The numbers 103 and 104 refers to the wire and the plug for connecting of the sensor 305 with the detection circuit 207.

When the press-knob 102 is pressed, the spring 303 gets compressed to put pressure on the sensor 305 to bend further leftwards while with the release of the pressure the spring helps the press-knob 102 to go back to its original position after relaxing the sensor 305. The leftward bend of the sensor 305 is already illustrated in the accompanying 2(b) and due to the variation in pressure on the press-knob due to hand tremor the leftward bending amount is varied causing a change in the output electrical resistance of the sensor 305 as an indication of the hand tremor.

Figure 5:
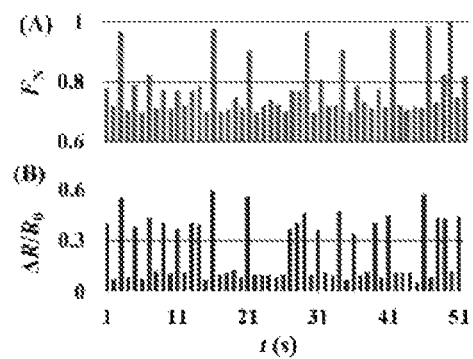
FIG. 5 shows the change in resistance due to the variation in force applied to the hand tremor detection system in accordance to a preferred embodiment of the present invention.
Figure 6:
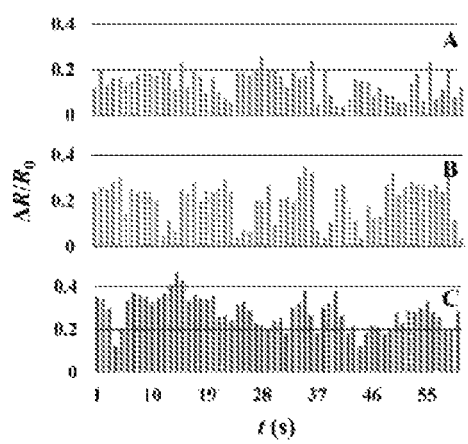
FIG. 6 shows the output of the sensor due to different level of tremor.

A typical response of the present system is described in the accompanying FIG. 5. The plots (A) and (B) describe the change in resistance with the change in force. The response of the sensor for mild, moderate, and high hand tremor is described in plots (A), (B), and (C) of the accompanying FIG. 6.

Figure 7:
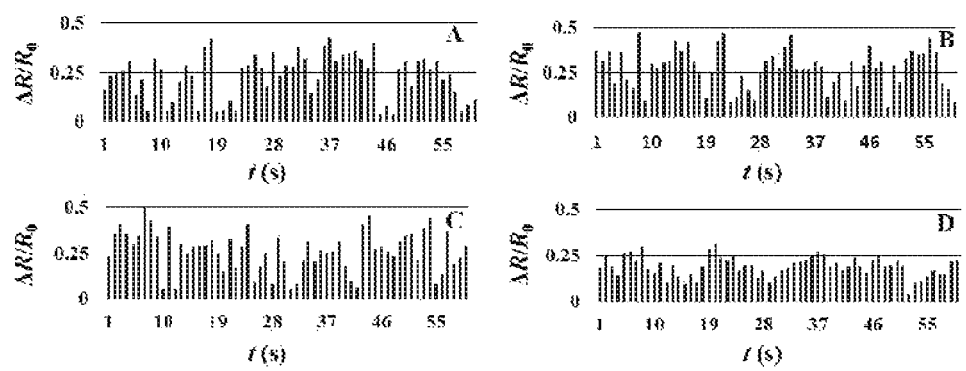
FIG. 7 shows the response of the sensor for four different patients.

In case of mild tremor, the ($R/R_0$) magnitude is less than 0.2 value whereas few ($R/R_0$) magnitude is beyond 0.2 in case of moderate tremor but in case of high tremor few ($R/R_0$) magnitude went beyond 0.4. Thus, from the amplitude of change in resistance the hand tremor levels can be measured. In order to detect the early stages of the neurological disorder a continuous monitoring of hand tremor for a span of few weeks can be performed with the proposed POCT device. For the diseased state, neurologist can be consulted when the response is already beyond the threshold limit. The accompanying FIG. 7 shows the change in resistance with time t for four different neurological patients having hand tremor with the present hand tremor detection system. Here $R_0$ refers to the base resistance of the sensor and R is the change in resistance.

It is well known that the tremor level of a patient is negligible and inconsistent at the early stage of the neurological disorders. Thus, a continuous and reliable detection of hand tremor for a prolonged duration is necessary to evaluate the early signs of the neurological disorders. However, modern life style does not allow the pathologically fit persons to spend time in the centralized testing centers or hospital for such a long period of time. Thus, to monitor continuously the very early stages of the neurological disorders it is essential to monitor them using some household devices. For this purpose, the processing unit of the present system includes the short distance communication device like Bluetooth module to transfer the measured data to a mobile interface. Further, with a specific android application the measured data can be monitored on the mobile phone itself and stored for future use and reference. In this process, measurements for longer duration can be performed for early detection of the neurological disorders.

We claim:

1. A portable hand tremor detection system comprising
a grasping means for holding by the a user with a resiliently biased pressing unit to put pressure on said resiliently biased pressing unit through the user's fingers when the user holds the grasping means;
a press sensitive sensor unit contained within said grasping means having operative communication with said resiliently biased pressing unit, wherein said press sensitive sensor unit comprises a pair of flexible conductive material coated polymer sheets, said pair of flexible conductive material coated polymer sheets is either maintained in spaced apart in relaxed condition indicative of no sensor signal or maintained in contact with one another in actuated condition indicative of generation of hand tremor sensor signal;
said resiliently biased pressing unit operatively connected to said pair of flexible conductive material coated polymer sheets for actuating the pair of flexible conductive material coated polymer sheets for said hand tremor based sensor signal generation upon vertical application of pressure on said resiliently biased pressing unit through the user's fingers;

a processing unit for processing said hand tremor based sensor signal for detecting the level of hand tremor of the user; and a cooperative power source, wherein said resiliently biased pressing unit includes a press-knob for receiving pressing force of the user and the press sensitive sensor unit is contained within said grasping means and is configured for sensing a vertical pressure applied on said press-knob;

wherein the pair of flexible conductive material coated polymer sheets is contained in said grasping means such that the vertically applied pressure on the press-knob resiliently bends the polymer sheets, wherein the pair of flexible conductive material coated polymer sheets includes two polymer sheets disposed in parallel configuration by a spacer, and conductive coatings on each polymer sheet side facing each other so that upon bending of the polymer sheets, the conductive coating of each polymer sheet of the pair comes in contact to each-other, whereby said conductive coatings on the polymer sheets are disposed in operative communication with a detection circuit of the processing unit through an electrical circuit connector, wherein the press knob is fixed on a movable support which is attached with a housing top of the grasping means under bias of a spring and an immovable support to form the resiliently biased press sensitive sensor unit configured to be compressed under the vertically applied pressure on said press knob which resiliently bends the pair of flexible conductive material coated polymer sheets and upon releasing or decreasing of the vertically applied pressure, the press-knob moves towards its original position under bias of the spring which relaxes the pair of flexible conductive material coated polymer sheets, whereby variation in the vertically applied pressure on the press-knob due to hand tremor changes an amount of bending of the pair of flexible conductive material coated polymer sheets which also changes contact area of the conductive coatings, resulting in a change in output electrical resistance of the pair of flexible conductive material coated polymer sheets as an indication of the hand tremor.

2. The portable hand tremor detection system as claimed in claim 1, wherein said processing unit is disposed in operative communication with said press sensitive sensor unit through a connecting wire and plug to receive the output electrical resistance of the press sensitive sensor unit and analyzes the output to determine the hand tremor level; and the portable hand tremor detection system further comprises LEDs on the grasping means and said processing unit for indicating their ON-OFF status.

3. The portable hand tremor detection system as claimed in claim 1, wherein the polymer sheets are made from polydimethylsiloxane (PDMS), and the conductive coatings thereon include reduced graphene oxide (RGO).

4. The portable hand tremor detection system as claimed in claim 1, wherein the polymer sheets bend in one direction under the vertically applied pressure on the press-knob, enabling the conductive coatings of the polymer sheets to come in contact with each other and act as an electrical resistor, whereby output resistance of said electrical resistor varies with change in the contact area of said conductive coatings.

5. The portable hand tremor detection system as claimed in claim 1, wherein the detection circuit is configured to track a change in the output electrical resistance and to generate an electronic signal for correlating with the hand tremor level of the user applying vertically applied pressure on the press-knob.

6. The portable hand tremor detection system as claimed in claim 1, wherein the grasping means includes
a hump structure to bend the pair of flexible conductive material coated polymer sheets within a housing of the grasping means.

7. The portable hand tremor detection system as claimed in claim 1, wherein the processing unit includes
the detection circuit comprising passive resistors (R1) and contact area resistor (RS) of the polymer sheets biased with a supply voltage;
an open source electronic development board; and
a short distance communication device;
wherein the detection circuit transmitted hand tremor indicating electronic signal includes the voltage across the flexible pressure sensor's contact area resistor $(R_S)$ represented as, $(R_S/R_S+R_1) \times V_S$ wherein, a change in the value of the $R_S$ cause a fluctuation of the voltage, whereby the detection circuit transmits the hand tremor indicating electronic signal to the electronic development board for converting it into a digital signal and the communication device forwards the digital signal to a connected display/computing device like mobile phone for further monitoring, processing and storing for future use and reference.

* * * * *